(12) United States Patent
Fukushima

(10) Patent No.: US 12,042,261 B2
(45) Date of Patent: Jul. 23, 2024

(54) IMAGING SUPPORT APPARATUS, MAGNETIC RESONANCE IMAGING APPARATUS, AND IMAGING SUPPORT METHOD

(71) Applicant: CANON MEDICAL SYSTEMS CORPORATION, Otawara (JP)

(72) Inventor: Masahiro Fukushima, Utsunomiya (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 672 days.

(21) Appl. No.: 17/009,174

(22) Filed: Sep. 1, 2020

(65) Prior Publication Data

US 2021/0068703 A1      Mar. 11, 2021

(30) Foreign Application Priority Data

Sep. 6, 2019   (JP) .................................. 2019-163265

(51) Int. Cl.
*A61B 5/055*      (2006.01)
*A61B 5/00*       (2006.01)
*A61B 5/11*       (2006.01)
*G06F 3/04886*    (2022.01)
(Continued)

(52) U.S. Cl.
CPC ............ *A61B 5/055* (2013.01); *A61B 5/1114* (2013.01); *A61B 5/458* (2013.01); *A61B 5/4585* (2013.01); *A61B 5/4595* (2013.01); *A61B 5/702* (2013.01); *A61B 5/743* (2013.01); *A61B 5/7445* (2013.01); *G06F 3/04886* (2013.01); *G06F 16/953* (2019.01); *G16H 30/40* (2018.01)

(58) Field of Classification Search
CPC ........ A61B 5/055; A61B 5/1114; A61B 5/743
See application file for complete search history.

(56) References Cited

U.S. PATENT DOCUMENTS 5,810,729 A * 9/1998 Hushek ................. A61B 5/055
                                                  324/309
2008/0253628 A1* 10/2008 Matsue ................. G16H 40/67
                                                  382/128
(Continued)

FOREIGN PATENT DOCUMENTS

JP       2018-008046 A      1/2018
KR   10-2013-0061573 A      6/2013

OTHER PUBLICATIONS

Japanese Office Action issued May 23, 2023 in Japanese Patent Application No. 2019-163265, 2 pages.

*Primary Examiner* — Jason M Ip
(74) *Attorney, Agent, or Firm* — Oblon, McClelland, Maier & Neustadt, L.L.P.

(57) ABSTRACT

An imaging support apparatus according to one embodiment includes an input interface and processing circuitry. The input interface receives input of first information about a disease or a case of a subject. The processing circuitry specifies, on the basis of the first information received by the input interface and second information in which the first information and posture information that expresses a posture of the subject suitable to perform imaging of the disease or the case are associated with each other, the posture information corresponding to the first information. Moreover, the processing circuitry causes a display to display the specified posture information.

13 Claims, 8 Drawing Sheets

(51) Int. Cl.
G06F 16/953 (2019.01)
G16H 30/40 (2018.01)

(56) References Cited

U.S. PATENT DOCUMENTS

2013/0055222 A1* 2/2013 Darrow .................... G06F 8/54
 717/140
2015/0081315 A1* 3/2015 Baker .................... G16H 30/20
 705/2
2016/0321427 A1* 11/2016 Bogoni ................. G16H 70/60

* cited by examiner

FIG.2

| ATTENTION REGION | POSTURE INFORMATION | COIL SETTING INFORMATION | IMAGING SURFACE INFORMATION ||| 
|---|---|---|---|---|---|
| | | | POSITION OF SLICE SECTION | SLICE THICKNESS | TILT OF SLICE SECTION |
| ANTERIOR CRUCIATE LIGAMENT | ·BEND KNEE BY XX DEGREES ·IMAGE DATA | ... | ... | ... | ... |
| MENISCUS | ... | ... | ... | ... | ... |
| KNEE CARTILAGE | ... | ... | ... | ... | ... |
| ... | | | | | |

FIG.3

| INFORMATION ABOUT DISEASE OR SYMPTOM | CANDIDATE FOR ATTENTION REGION |
|---|---|
| KNEE HURTS | ANTERIOR CRUCIATE LIGAMENT |
|  | MENISCUS |
|  | ... |
| DAMAGE IN ANTERIOR CRUCIATE LIGAMENT | ANTERIOR CRUCIATE LIGAMENT |
| ANKLE HURTS | ... |
| ⋮ | ⋮ |

CANDIDATE FOR ATTENTION REGION

80

20a: MENISCUS
20b: XX CARTILAGE
20c: ANTERIOR CRUCIATE LIGAMENT
20d: yy LIGAMENT

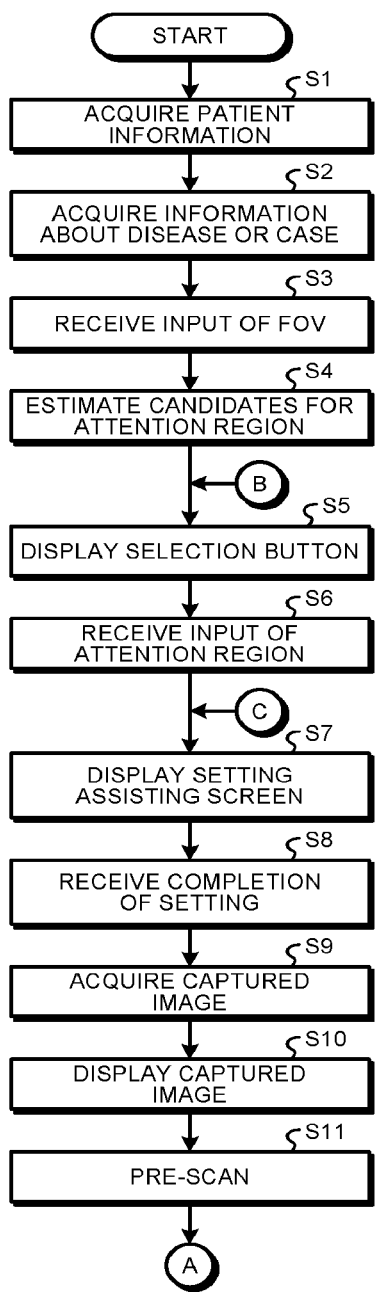

FIG.9

| INFORMATION ABOUT DISEASE OR CASE | CANDIDATE FOR ATTENTION REGION | POSTURE INFORMATION | COIL SETTING INFORMATION | POSITION OF SLICE SECTION | SLICE THICKNESS | TILT OF SLICE SECTION |
|---|---|---|---|---|---|---|
| KNEE HURTS | ANTERIOR CRUCIATE LIGAMENT | ·BEND KNEE BY xx DEGREES<br>·IMAGE DATA | ⋮ | ⋮ | ⋮ | ⋮ |
|  | MENISCUS | ⋮ | ⋮ | ⋮ | ⋮ | ⋮ |
| DAMAGE IN ANTERIOR CRUCIATE LIGAMENT | ANTERIOR CRUCIATE LIGAMENT | ·BEND KNEE BY xx DEGREES<br>·IMAGE DATA | ⋮ | ⋮ | ⋮ | ⋮ |
| ANKLE HURTS | ⋮ | ⋮ | ⋮ | ⋮ | ⋮ | ⋮ |
| ⋯ | ⋯ | ⋯ | ⋯ | ⋯ | ⋯ | ⋯ |

1090

IMAGING SUPPORT APPARATUS, MAGNETIC RESONANCE IMAGING APPARATUS, AND IMAGING SUPPORT METHOD

CROSS-REFERENCE TO RELATED APPLICATIONS

This application is based upon and claims the benefit of priority from Japanese Patent Application No. 2019-163265, filed on Sep. 6, 2019; the entire contents of which are incorporated herein by reference.

FIELD

Embodiments described herein relate generally to an imaging support apparatus, a magnetic resonance imaging apparatus, and an imaging support method.

BACKGROUND

Conventionally, in a case of imaging of a patient with a magnetic resonance imaging (MRI) apparatus, for example, a technologist works to fix the patient's posture. How the imaged part is drawn in the MR image is different depending on the patient's posture at the time of the imaging. For this reason, when the technologist fixes the patient, it has been necessary to decide the patient's posture with a careful consideration. If the patient is not fixed with the proper posture, it may be necessary to image the MR image again.

BRIEF DESCRIPTION OF THE DRAWINGS

FIG. 2 is a diagram illustrating one example of imaging assistant information according to one embodiment;

FIG. 3 is a diagram illustrating one example of attention region candidate information according to one embodiment;

FIG. 4 is a diagram illustrating one example of an attention region selecting screen displayed on a display according to one embodiment;

FIG. 8A is a flowchart illustrating one example of the procedure of an imaging assist process according to one embodiment;

FIG. 9 is a diagram illustrating one example of imaging assistant information according to a third modification.

DETAILED DESCRIPTION

Embodiments of an imaging support apparatus, a magnetic resonance imaging apparatus, and an imaging support method are hereinafter described in detail with reference to the drawings.

The imaging support apparatus according to the embodiment includes an input interface and processing circuitry. The input interface receives input of first information about a disease or a case of a subject. On the basis of the first information received from the input interface and second information in which the first information and posture information expressing the posture of the subject that is suitable for imaging of the disease or the case are associated with each other, the processing circuitry specifies the posture information corresponding to the first information. In addition, the processing circuitry causes a display to display the specified posture information.

Figure 1:
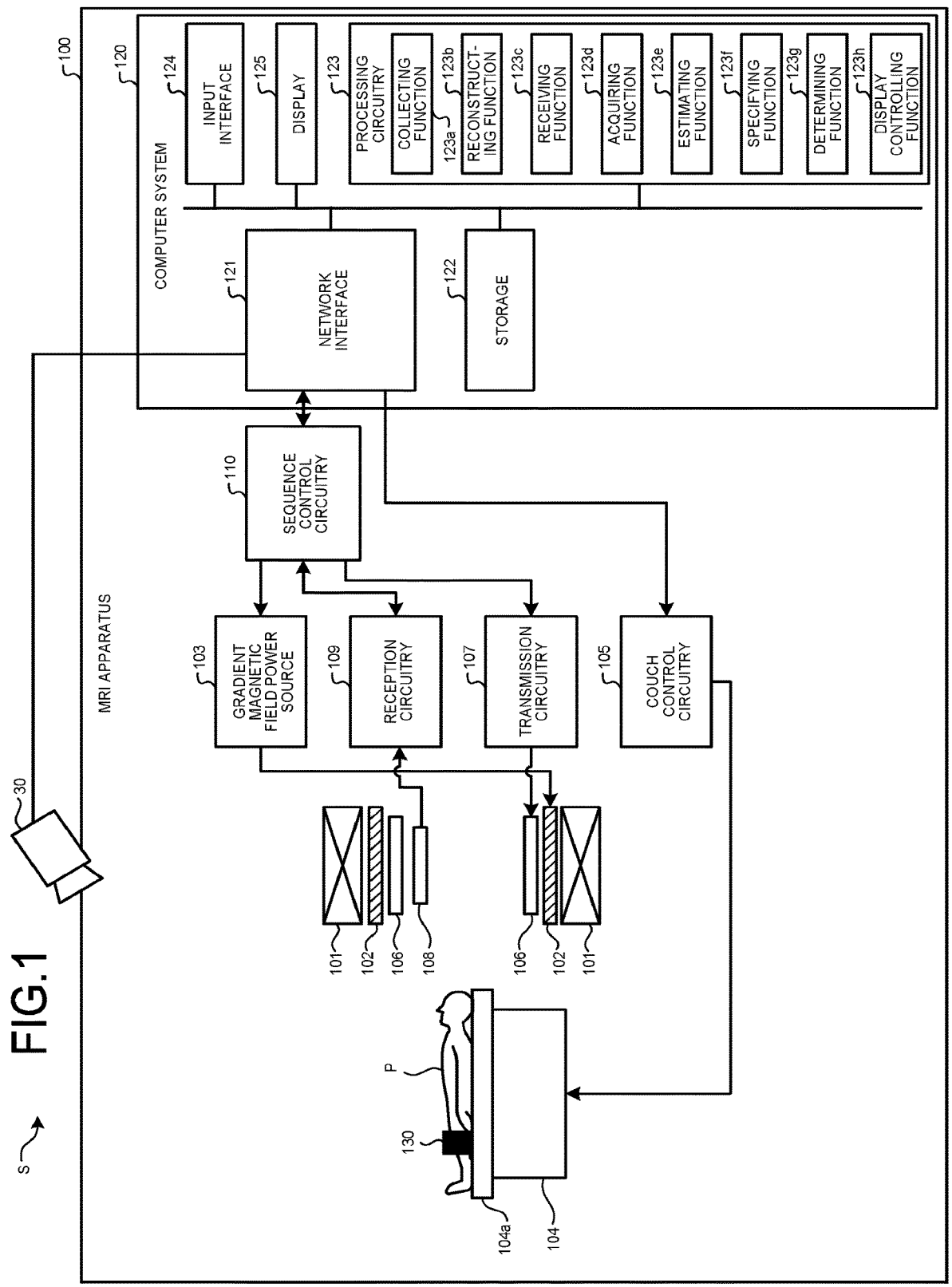
FIG. 1 is a block diagram illustrating a structure of a system according to one embodiment.

FIG. 1 is a block diagram illustrating a structure of a system S according to the present embodiment. The system S includes an MRI (Magnetic Resonance Imaging) apparatus 100 and a camera 30.

The camera 30 captures an image of a subject P placed on a couchtop 104a, which is described below. The timing when the image is captured by the camera 30 is after the subject P is fixed on the couchtop 104a, for example. The camera 30 sends the captured image to a computer system 120 of the MRI apparatus 100. The captured image, which is a still picture in the present embodiment, may be a moving picture.

The MRI apparatus 100 includes a static magnetic field magnet 101, a gradient coil 102, a gradient magnetic field power source 103, a couch 104, couch control circuitry 105, a transmission coil 106, transmission circuitry 107, a reception coil 108, reception circuitry 109, sequence control circuitry 110, the computer system 120, a gantry 150, and a local RF coil 130. Note that the MRI apparatus 100 does not include the subject P. The subject P is, for example, a patient whose MR image is imaged by the MRI apparatus 100. The MRI apparatus 100 is one example of the imaging support apparatus in the present embodiment.

The static magnetic field magnet 101 is a magnet formed to have a hollow cylindrical shape (including the shape whose cross section orthogonal to the axis of the cylinder is elliptical), and generates a uniform static magnetic field in the internal space.

The gradient coil 102 is a coil formed to have a hollow cylindrical shape (including the shape whose cross section orthogonal to the axis of the cylinder is elliptical), and generates a gradient magnetic field. The gradient coil 102 is formed by a combination of three coils corresponding to axes X, Y, and Z that are orthogonal to each other, and these three coils having received the current supplied individually from the gradient magnetic field power source 103 generates the gradient magnetic field whose magnetic field intensity changes along the axes X, Y, and Z.

The gradient magnetic field power source 103 supplies current to the gradient coil 102. For example, the gradient magnetic field power source 103 supplies current individually to each of the three coils included in the gradient coil 102.

The couch 104 includes the couchtop 104a on which the subject P is placed, and under the control of the couch control circuitry 105, the couchtop 104a is inserted into a cavity (imaging port) of the gradient coil 102 with the subject P placed on the couchtop 104a. The couch control circuitry 105 is a processor that moves the couchtop 104a in a longitudinal direction and a vertical direction by driving the couch 104 under the control of the computer system 120.

The transmission coil 106 is disposed inside the gradient coil 102, and upon the reception of a radio frequency (RF) signal supplied from the transmission circuitry 107, applies a high-frequency magnetic field to the subject P. As the high-frequency magnetic field is applied by the transmission coil 106, the subject P is excited. A region where the high-frequency magnetic field is applied by the transmission coil 106 is, for example, a field of view (FOV). The FOV is one example of a region to be excited in the present embodiment.

The transmission circuitry 107 supplies, to the transmission coil 106, an RF pulse corresponding to the Larmor frequency that is determined depending on the kind of atomic nucleus to be an object and the intensity of the magnetic field under the control of the sequence control circuitry 110.

The reception coil 108 is disposed inside the gradient coil 102, and receives a magnetic resonance signal (hereinafter referred to as MR signal) generated from the subject P due to the influence of the high-frequency magnetic field. Upon the reception of the MR signal, the reception coil 108 outputs the received MR signal to the reception circuitry 109. Note that the reception coil 108 is provided separately from the transmission coil 106 in FIG. 1; however, this is merely one example and the structure is not limited to this example. In another example, the reception coil 108 may also serve as the transmission coil 106.

The reception circuitry 109 performs analog-digital conversion on the analog MR signal output from the reception coil 108, thereby generating MR data. The reception circuitry 109 transmits the generated MR data to the sequence control circuitry 110. Note that the analog-digital conversion may be performed in the reception coil 108. In addition, the reception circuitry 109 can perform an arbitrary signal process other than the analog-digital conversion.

The local RF coil 130 is attached to an imaging part of the subject P by a technologist, for example, and receives the MR signal generated from the subject P. The local RF coil 130 outputs the received MR signal to the reception circuitry 109.

The local RF coil 130 may be selected from various kinds including a coil for a knee, a coil for an ankle, and a coil for an elbow in accordance with the imaging part. In the example illustrated in FIG. 1, the local RF coil 130 is a coil for a knee; however, the local RF coil 130 is not limited to the coil for a knee. Note that the local RF coil 130 may further have a function of the transmission coil that applies the RF pulse to the subject P.

In the present embodiment, the transmission coil 106 is one example of the RF coil. In addition, the local RF coil 130 may be one example of the RF coil.

The sequence control circuitry 110 performs the imaging of the subject P by controlling the gradient magnetic field power source 103, the transmission circuitry 107, and the reception circuitry 109 on the basis of the sequence information transmitted from the computer system 120. In addition, the sequence control circuitry 110 receives the MR data from the reception circuitry 109. The sequence control circuitry 110 transfers the received MR data to the computer system 120.

The sequence control circuitry 110 may be achieved by a processor, or by a combination of software and hardware, for example.

The sequence information is information that defines the procedure for the imaging. The sequence information is generated by the computer system 120 on the basis of the imaging condition designated by the operator, such as the selected excitation position, the repetition time (TR), the echo time (TE), the position of the slice section, the slice thickness, the tilt of the slice section, the Field Of View (FOV), and many other imaging parameters.

The computer system 120 performs the entire control over the MRI apparatus 100, the data collection, the image reconstruction, and so on. The computer system 120 includes a network interface 121, storage 122, processing circuitry 123, an input interface 124, and a display 125.

The network interface 121 transmits the sequence information to the sequence control circuitry 110, and receives the MR data from the sequence control circuitry 110. The MR data received by the network interface 121 is stored in the storage 122.

In addition, the network interface 121 acquires information about the disease or the case of the subject P. For example, the network interface 121 acquires information about the disease or the case of the subject P from a hospital information system (HIS) or a radiology information system (RIS) outside the MRI apparatus 100 through a hospital intranet or the like.

The information about the disease or the case includes one of, or both the information about the disease and the information about the case. In the present embodiment, the information about the disease is, for example, the name of the sickness and injuries. Examples of the information about the disease include "medial meniscus injury" and "anterior cruciate ligament (ACL)". The information about the case is, for example, a symptom such as chief complaint. One example of the information about the case is "my knee hurts when I bend it". The information about the case may include the symptom other than the subjective symptoms of the patient.

The network interface 121 acquires the patient information about the age, physique, and the like of the subject P from HIS or RIS, for example.

The network interface 121 sends the information about the disease or the case of the subject P and the patient information having been acquired, to the processing circuitry 123. In addition, the network interface 121 may save the information about the disease or the case of the subject P and the patient information having been acquired, in the storage 122.

Moreover, the network interface 121 acquires, from the camera 30, the captured image of the subject P placed on the couchtop 104a. The network interface 121 sends the acquired image to the processing circuitry 123. In addition, the network interface 121 may save the acquired image in the storage 122.

The storage 122 stores various computer programs. The storage 122 is achieved by, for example, a semiconductor memory element such as a random access memory (RAM) or a flash memory, a hard disk, or an optical disk. Note that the storage 122 may be used as a non-transitory storage medium by hardware. The storage 122 is one example of storage or a memory.

Moreover, the storage 122 stores imaging assistant information. The imaging assistant information is one example of second information in the present embodiment.

FIG. 2 is a diagram illustrating one example of imaging assistant information 90 in the present embodiment. In the example illustrated in FIG. 2, the imaging assistant information 90 is a database in which an attention region, posture information, coil setting information, and imaging surface information are associated with each other. The imaging assistant information 90 is not limited to this structure, and at least the attention region and the posture information are associated with each other.

The attention region is a region to which attention should be paid for diagnosing the disease or the case, and is narrower than the FOV. The attention region is different depending on the disease or the case. For example, if the FOV is "knee", the attention region may be "anterior cruciate ligament", "meniscus", or "knee cartilage" depending on the disease or the case. In the present embodiment, the information expressing the attention region is one example of the first information. The attention region may be, for example, a region of interest (ROI).

The posture information expresses the posture of the subject P that is suitable to perform imaging of the disease or the case. For example, the posture information expresses the posture of the subject P that enables the imaging of the attention region included in the FOV. More specifically, the posture information is information about the posture of a joint part of the subject P.

The information about the posture of the joint part of the subject P is, for example, the information expressing the bending angle of the joint of the subject P.

The posture information may be registered as text information or may be registered as image data that illustrates the posture of the subject P.

The coil setting information is information expressing the kind of local RF coil 130 that is attached to the subject P and the attaching position thereof. Note that if the local coil is not used in the imaging, the unnecessity of the attachment of the local coil is registered as the coil setting information.

The posture information and the coil setting information may be registered as the text information or may be registered as the image data that illustrates the posture of the subject P or the position of attaching the local RF coil 130.

In the present embodiment, the simple term "setting" includes both fixing the subject P and setting the local RF coil 130 to the subject P.

The imaging surface information is information about the slice section where the attention region can be imaged. The imaging surface information includes, for example, the position of the slice section, the slice thickness, and the tilt of the slice section in the imaging of the subject P. The position and the tilt of the slice section are defined based on, for example, the characteristic point such as a bone of the subject P in the FOV. The imaging surface information illustrated in FIG. 2 is one example, and the imaging surface information is not limited to the content therein. In addition, the slice section is one example of the imaging surface in the present embodiment.

The imaging assistant information 90 may be registered by an operator or acquired from an external device.

In addition, the storage 122 further stores therein attention region candidate information in which the information about the disease or the case and the attention region candidate are associated with each other.

FIG. 3 is a diagram illustrating one example of attention region candidate information 91 according to the present embodiment. As illustrated in FIG. 3, the attention region candidate information 91 is a database in which a plurality of pieces of information about the disease or the case and one or more attention region candidates are associated with each other. The structure of the attention region candidate information 91 illustrated in FIG. 3 is one example, and the structure of the attention region candidate information 91 is not limited to the illustrated one.

Back to FIG. 1, the input interface 124 receives various instructions or the input of information from the operator, for example a doctor or a radiologist. The input interface 124 is achieved by, for example, a trackball, a switch button, a mouse, a keyboard, or the like.

Note that the input interface 124 in the present embodiment is not limited to the input interface including a physical operation component such as a mouse or a keyboard. One example of the input interface 124 is processing circuitry that receives an electric signal corresponding to an input operation from an external input device provided separately from the MRI apparatus 100 and outputs the electric signal to the processing circuitry 123.

In addition, the input interface 124 receives the input of the attention region corresponding to the disease or the case of the subject P. For example, the input interface 124 receives the input of the attention region by receiving the fact that the operator has pushed any of a plurality of selection buttons displayed on the display 125 by a display controlling function 123h, which is described below.

In addition, the input interface 124 receives the operator's input of the information expressing the FOV of the subject P.

Moreover, the input interface 124 receives the operation of changing or deciding the slice section by the operator. Furthermore, the input interface 124 receives the input of completion of the setting from the operator.

The input interface 124 is connected to the processing circuitry 123. After converting various input operations received from the operator into the electric signal, the input interface 124 outputs the electric signal to the processing circuitry 123.

The display 125 displays various Graphical User Interfaces (GUIs), MR (Magnetic Resonance) images, various images generated by the processing circuitry 123, and the like under the control of the processing circuitry 123. The display 125 is one example of the display.

The processing circuitry 123 performs the entire control of the MRI apparatus 100. More specifically, the processing circuitry 123 includes a collecting function 123a, a reconstructing function 123b, a receiving function 123c, an acquiring function 123d, an estimating function 123e, a specifying function 123f, a determining function 123g, and the display controlling function 123h. The collecting function 123a is one example of a collector. Furthermore, a process performed by the collecting function 123a is referred to as a collecting step. Note that the collecting function 123a may be divided into an applying function and a collecting function. In addition, a process performed by the collecting function 123a may be divided into an applying step and a collecting step. The reconstructing function 123b is one example of a reconstructor. Furthermore, a process performed by the reconstructing function 123b is referred to as a reconstructing step. The receiving function 123c is one example of a receiver. Furthermore, a process performed by the receiving function 123c is referred to as a receiving step. The acquiring function 123d is one example of an acquirer. A process performed by the acquiring function 123d is referred to as an acquiring step. The estimating function 123e is one example of an estimator. A process performed by the estimating function 123e is referred to as an estimating step. The specifying function 123f is one example of a specifier. A process performed by the specifying function 123f is referred to as a specifying step. The determining function 123g is one example of a determiner. A process performed by the determining function 123g is referred to as a determining step. The display controlling function 123h is one example of a display controller. A process performed by the display controlling function 123h is referred to as a displaying step.

Here, for example, the components of the processing circuitry 123 including the collecting function 123a, the reconstructing function 123b, the receiving function 123c, the acquiring function 123d, the estimating function 123e, the specifying function 123f, the determining function 123g, and the display controlling function 123h are stored in the storage 122 in a form of a computer program that can be executed by a computer. The processing circuitry 123 reads out each computer program from the storage 122, and executes the read computer program, thereby achieving the function corresponding to the computer program. In other words, the processing circuitry 123 that has read out the computer program has the function illustrated in the processing circuitry 123 in FIG. 1. Note that, in FIG. 1, one processing circuitry 123 achieves each processing function of the collecting function 123a, the reconstructing function 123b, the receiving function 123c, the acquiring function 123d, the estimating function 123e, the specifying function 123f, the determining function 123g, and the display controlling function 123h; however, the processing circuitry 123 may be formed by combining a plurality of independent processors. In this case, each processing function may be achieved by having each processor execute the computer program.

The term "processor" used above refers to, for example, a Central Processing Unit (CPU), a Graphics Processing Unit (GPU), an Application Specific Integrated Circuit (ASIC), a programmable logic device (for example, Simple Programmable Logic Device (SPLD)), a Complex Programmable Logic Device (CPLD), and a Field Programmable Gate Array (FPGA). Note that instead of saving the computer program in the storage 122, the computer program may be directly incorporated in the circuitry of the processor. In this case, the processor achieves the function by reading and executing the computer program incorporated in the circuitry.

The collecting function 123a collects the MR data, which is converted from the MR signal generated when the pulse sequence is executed, from the sequence control circuitry 110 through the network interface 121 by executing various pulse sequences.

More specifically, the collecting function 123a generates the imaging parameters suitable to perform imaging of the subject P on the basis of the FOV and the attention region that are received by the receiving function 123c, which is described below, the patient information acquired by the network interface 121, the position of the slice section, the slice thickness, and the tilt of the slice section.

The position of the slice section, the slice thickness, and the tilt of the slice section correspond to the position of the slice section, the slice thickness, and the tilt of the slice section that are specified by the specifying function 123f, which is described below, or the position of the slice section, the slice thickness, and the tilt of the slice section that are input by the operator.

The collecting function 123a changes the imaging parameter in accordance with the age or physique of the subject P included in the patient information, for example. The collecting function 123a may generate the imaging parameter suitable to perform imaging of the subject P on the basis of the information about the disease or the case of the subject P that is acquired by the network interface 121.

The collecting function 123a generates the sequence information on the basis of the decided imaging parameter. The collecting function 123a sends the generated sequence information to the sequence control circuitry 110 through the network interface 121.

The collecting function 123a arranges the collected MR data in accordance with the phase encoding quantity or the frequency encoding quantity that is applied by the gradient magnetic field. The MR data that is arranged in a k space is referred to as k spatial data. The k spatial data is saved in the storage 122.

The reconstructing function 123b generates the magnetic resonance image by performing a reconstructing process, such as Fourier transformation, on the k spatial data stored in the storage 122. The reconstructing function 123b saves the generated magnetic resonance image in the storage 122.

The receiving function 123c receives various operations of the operator through the input interface 124. For example, the receiving function 123c receives the input of the attention region or the FOV through the input interface 124. The receiving function 123c sends the received attention region to the specifying function 123f. In addition, the receiving function 123c sends the received FOV to the collecting function 123a.

Moreover, the receiving function 123c receives the operator's operation for accepting or changing the position of the slice section, the slice thickness, or the tilt of the slice section that is specified by the specifying function 123f that is described below. The receiving function 123c sends the received content of the operation to the collecting function 123a.

The receiving function 123c receives the input of the completion of the setting from the operator through the input interface 124. The receiving function 123c notifies the acquiring function 123d that the input of the completion of the setting has been received.

The acquiring function 123d acquires the patient information, and the information about the disease or the case of the subject P acquired by the network interface 121. The acquiring function 123d sends the acquired information about the disease or the case of the subject P to the estimating function 123e. The acquiring function 123d sends the acquired patient information of the subject P to the collecting function 123a.

The acquiring function 123d acquires the captured image acquired by the network interface 121. The acquiring function 123d sends the acquired image to the display controlling function 123h.

The estimating function 123e estimates one or more candidates for the attention region, from the information about the disease or the case. More specifically, the estimating function 123e searches the attention region candidate information 91 saved in the storage 122 for one or more candidates for the attention region that are associated with the information about the disease or the case of the subject P that is acquired by the acquiring function 123d.

In addition, the estimating function 123e may narrow down the candidates for the attention region on the basis of the FOV received by the receiving function 123c. The estimating function 123e sends one or more candidates for the attention region obtained as the search result to the display controlling function 123h as a result of estimating the candidate for the attention region.

The specifying function 123f specifies the posture information corresponding to the attention region on the basis of the attention region received by the input interface 124 and the imaging assistant information 90. More specifically, the specifying function 123f searches for the posture information associated with the attention region received by the input interface 124 from the imaging assistant information 90 stored in the storage 122. The specifying function 123f sends the search result to the display controlling function 123h. The timing when the specifying function 123f specifies the posture information is before pre-scanning is performed, for example. The pre-scanning is, for example, scanning for acquiring the MR image with low resolution to decide the FOV, scanning for acquiring sensitivity information of the reception coil 108, or scanning for acquiring the information to correct the unevenness of the MR image.

Moreover, after the pre-scanning of the subject P, the specifying function 123f specifies the position of the slice section associated with the attention region received by the input interface 124, from the imaging assistant information 90. Furthermore, from the imaging assistant information 90, the specifying function 123f specifies the slice thickness and the tilt of the slice section that are associated with the attention region received by the input interface.

The position of the slice section, the slice thickness, and the tilt of the slice section that are specified by the specifying function 123f are the position of the slice section, the slice thickness, and the tilt of the slice section that are recommended when the attention region received by the input interface 124 is imaged. The position of the slice section, the slice thickness, and the tilt of the slice section that are recommended are referred to as a recommended slice section when they are collectively called. The specifying function 123f sends the position of the slice section, the slice thickness, and the tilt of the slice section that are specified, to the determining function 123g and the display controlling function 123h.

The determining function 123g determines whether the attention region can be imaged on the basis of the posture of the subject P, the sensitivity of the local RF coil 130, the sensitivity of the reception coil 108, and the like in the pre-scanning of the subject P. Specifically, the determining function 123g determines whether the recommended slice section that is specified by the specifying function 123f can be set on the attention region of the subject P drawn on the magnetic resonance image imaged in the pre-scanning. Since the magnetic resonance image imaged in the pre-scanning is used to position the slice section on a slice decision assisting screen, which is described below, the magnetic resonance image is hereinafter referred to as a locator image.

For example, the determining function 123g aligns the position, the thickness, and the tilt that are suitable to the recommended slice section specified by the specifying function 123f on the basis of the characteristic point such as a bone of the subject P drawn in the locator image. The recommended slice section is the slice section where the attention region can be imaged; therefore, if the slice section can be formed with the position, the thickness, and the tilt suitable to the recommended slice section on the locator image, the determining function 123g determines that the attention region can be imaged.

Furthermore, if the slice section cannot be formed with the position, the thickness, and the tilt suitable to the recommended slice section on the locator image, the determining function 123g determines that the attention region cannot be imaged. For example, if the attention region cannot be drawn on the locator image because the posture of the subject P is not the posture that enables the imaging of the attention region, the recommended slice section and the subject P drawn on the locator image cannot be aligned in position and thus, the recommended slice section cannot be formed on the locator image. In another example, if the sensitivity of the local RF coil 130 or the sensitivity of the reception coil 108 is insufficient, the determining function 123g cannot extract the characteristic point such as a bone of the subject P from the locator image, and the recommended slice section cannot be formed on the locator image.

The determining function 123g sends a result of determining whether the imaging of the attention region is possible to the display controlling function 123h.

Note that the method of determining whether the imaging of the attention region is possible is not limited to the aforementioned example, and the determining function 123g can employ various image processing methods.

The display controlling function 123h causes the display 125 to display one or more selection buttons expressing one or more candidates for the attention region in accordance with the disease or the case of the subject P. In the present embodiment, the screen including one or more selection buttons is referred to as an attention region selecting screen.

FIG. 4 is a diagram illustrating one example of an attention region selecting screen 80 that is displayed on the display 125 according to the present embodiment. Each of selection buttons 20a to 20d in FIG. 4 (hereinafter referred to as selection button 20 simply unless they need to be distinguished) is a candidate for the attention region estimated by the estimating function 123e. In FIG. 4, the display controlling function 123h displays the four selection buttons 20; however, the number of selection buttons 20 is not limited to four. In addition, the selection button 20 is one example of the button in the present embodiment.

For example, when any of the above selection buttons 20 on the attention region selecting screen 80 is pushed by the operator's mouse operation or the like, the input interface 124 receives the input of the attention region corresponding to the pushed selection button 20.

Furthermore, the display controlling function 123h causes the display 125 to display the posture information specified by the specifying function 123f. In the present embodiment, the screen expressing the posture information is referred to as a setting assisting screen. The setting assisting screen is displayed when, for example, the technologist fixes the subject P at the position suitable for the imaging before the pre-scanning is performed.

Figure 5:
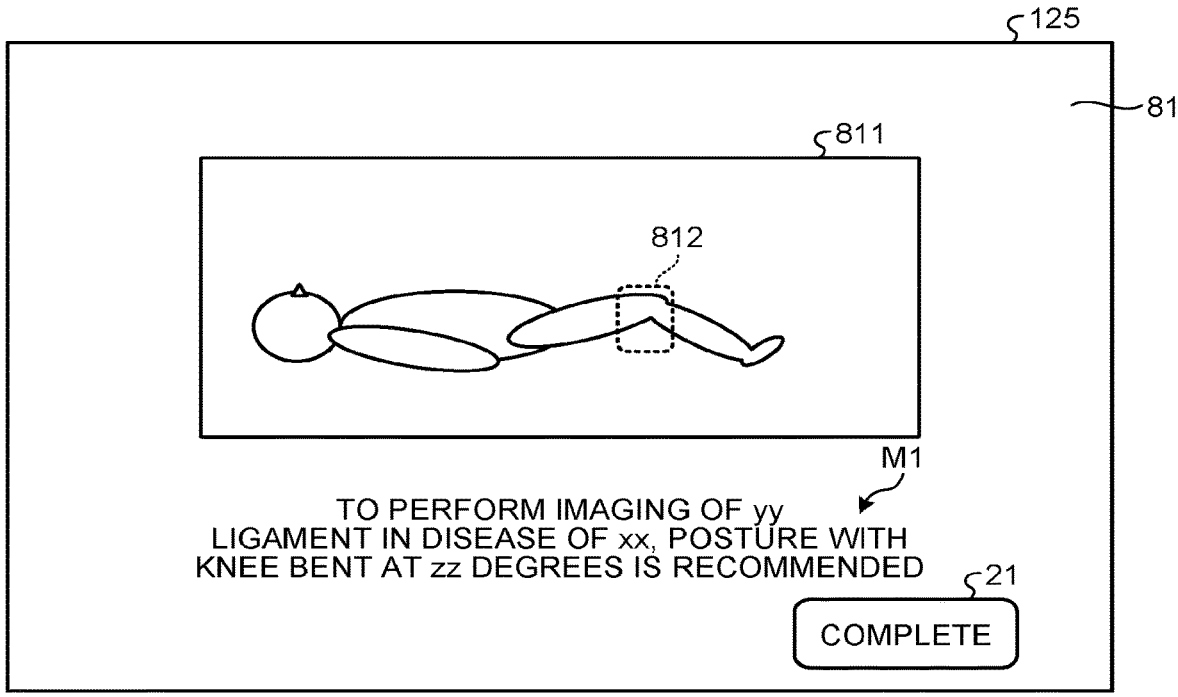
FIG. 5 is a diagram illustrating one example of a setting assisting screen displayed on the display according to the embodiment.

FIG. 5 is a diagram illustrating one example of a setting assisting screen 81 that is displayed on the display 125 according to the present embodiment. On the setting assisting screen 81, a model image 811 expressing the posture of the subject P that enables the imaging of the attention region that is selected by the operator is displayed. The model image 811 is, for example, the image data that is registered as the posture information in the imaging assistant information 90. The model image 811 expresses, for example, the bending angle of the joint of the subject P. Although the model image 811 expresses the entire body of the subject P in FIG. 5, the model image 811 may express a part of the subject P. In addition, the model image 811 may be a picture as illustrated in FIG. 5, or may be the MR image imaged in the past or the image obtained by a camera.

In addition, the display controlling function 123h displays an icon 812, which expresses the local RF coil 130 set to the subject P, in a manner of overlapping with the image expressing the subject P on the model image 811. For example, the display controlling function 123h displays the icon 812, which corresponds to the kind of local RF coil 130 defined in the coil setting information registered in the imaging assistant information 90, at the position corresponding to the position defined in the coil setting information where the local RF coil 130 is attached. In the example illustrated in FIG. 5, the display controlling function 123h displays the local RF coil 130 for a knee at the position corresponding to the knee of a person image on the model image 811.

Moreover, the display controlling function 123h displays, on the setting assisting screen 81, a message M1 describing the posture of the subject P that enables the imaging of the attention region that is selected by the operator. The message M1 includes the content registered as the posture information in the imaging assistant information 90, for example. Note that the display controlling function 123h may display only one of the model image 811 and the message M1. Furthermore, in a case where the use of the local RF coil 130 is not recommended to perform imaging of the attention region selected by the operator, the display controlling function 123h may display on the setting assisting screen 81, the message M1 additionally expressing that the local RF coil 130 is not attached to the subject P.

Moreover, the display controlling function 123h displays on the setting assisting screen 81, a completion button 21 with which the operator inputs the completion of setting by the technologist, for example. When the completion button 21 has been pushed by the mouse operation of the operator, for example, the input interface 124 receives the input of the completion of the setting.

Note that the setting assisting screen 81 illustrated in FIG. 5 is one example, and the display controlling function 123h may display more specific information about the setting. For example, the kind of fixing tool to make the posture suitable to perform imaging of the subject P may be displayed. Examples of the fixing tool include a pad and a mattress.

The display controlling function 123h causes the display 125 to display the captured image of the subject P acquired by the acquiring function 123d after the setting of the subject P. By recognizing the captured image visually, the operator checks if the posture of the subject P or the attaching position of the local RF coil 130 coincides with the posture information or the coil setting information displayed on the setting assisting screen 81. For example, the display controlling function 123h may cause the display 125 to display the captured image of the subject P and the model image 811 side by side.

If the determining function 123g has determined that the attention region can be imaged after the subject P is pre-scanned, the display controlling function 123h causes the display 125 to display the position of the slice section, the slice thickness, and the tilt of the slice section that are specified by the specifying function 123f. In the present embodiment, the screen displaying the position of the slice section, the slice thickness, and the tilt of the slice section that are specified by the specifying function 123f is referred to as a slice decision assisting screen.

Note that the display controlling function 123h may display not all but one or more of the position of the slice section, the slice thickness, and the tilt of the slice section. For example, the display controlling function 123h may display only the position of the slice section.

Figure 6:
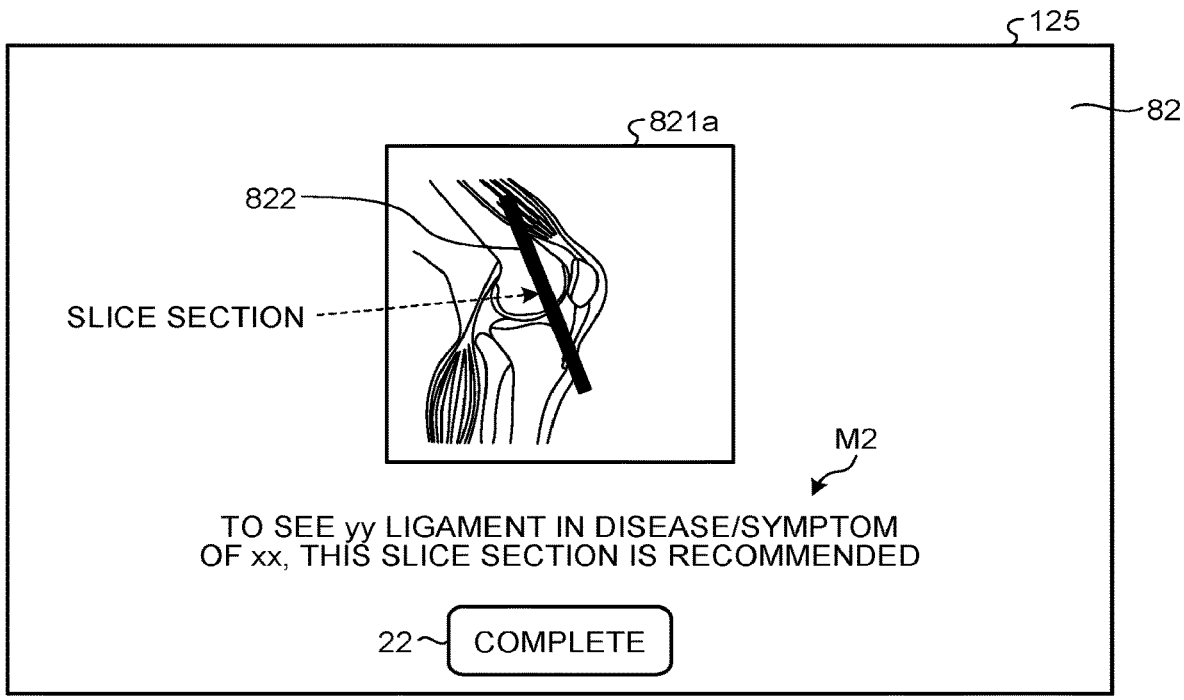
FIG. 6 is a diagram illustrating one example of a slice decision assisting screen 82 displayed on the display according to the embodiment.

FIG. 6 is a diagram illustrating one example of a slice decision assisting screen 82 displayed on the display 125 according to the present embodiment. The display controlling function 123h displays a slice reference image 822 expressing the recommended slice section on a locator image 821a imaged by the pre-scanning. The position, the thickness, and the tilt of the slice reference image 822 are the position, the thickness, and the tilt of the slice section that are specified by the specifying function 123f.

The display controlling function 123h displays on the slice decision assisting screen 82, a message M2 describing the recommended slice section. Note that the message M2 may be text containing numerals of the thickness of the slice section specified by the specifying function 123f, for example.

On the slice decision assisting screen 82, the operator can operate to change the position, the thickness, or the tilt of the slice reference image 822.

The display controlling function 123h displays a decision button 22 on the slice decision assisting screen 82. The decision button 22 can receive a decision operation for the user to decide to use, in the imaging, the position, the thickness, and the tilt of the slice section expressed by the slice reference image 822 displayed on the slice decision assisting screen 82.

For example, when the decision button 22 is pushed by the operator's mouse operation or the like, the input interface 124 receives the position, the slice thickness, and the tilt of the slice section displayed on the slice decision assisting screen 82 as the decided definition information of the slice section.

For example, to accept the recommended slice section, the operator pushes the decision button 22 without moving the slice reference image 822 displayed on the slice decision assisting screen 82. When the operator wants to perform imaging of the slice section other than the recommended slice section, the operator pushes the decision button 22 after changing the position, the thickness, or the tilt of the slice reference image 822.

If the determining function 123g has determined that the imaging of the attention region is impossible after the subject P is pre-scanned, the display controlling function 123h causes the display 125 to display a notification screen notifying that the imaging of the attention region is impossible.

Figure 7:
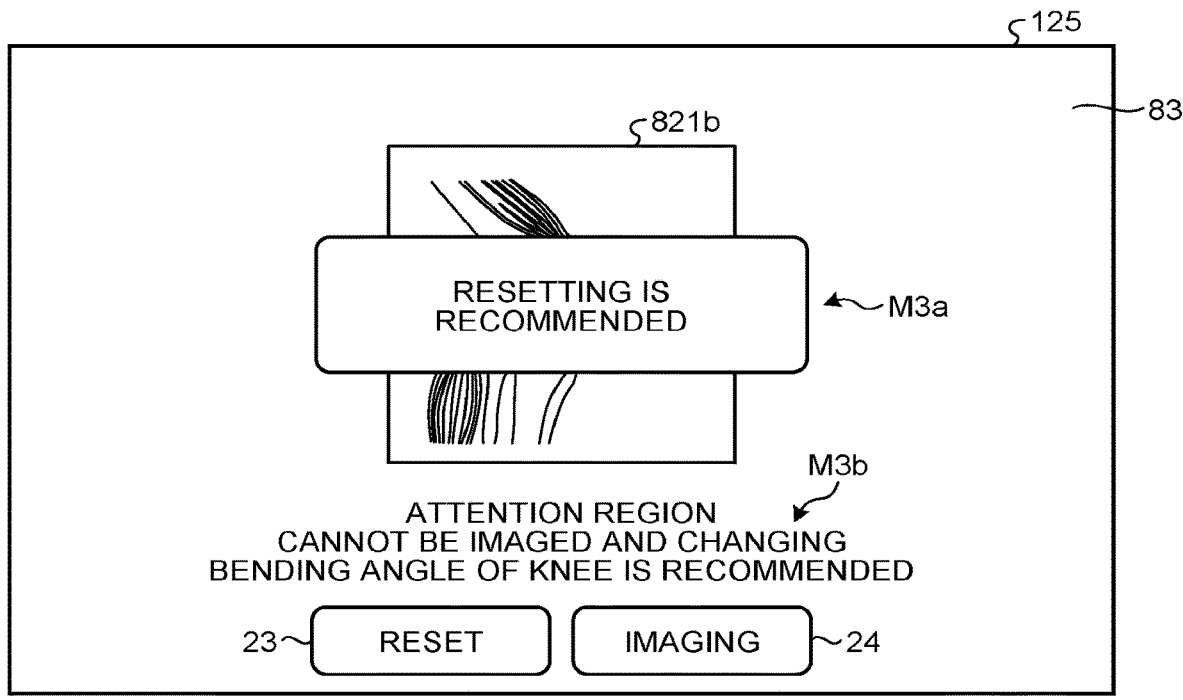
FIG. 7 is a diagram illustrating one example of a notification screen displayed on the display according to the embodiment.

FIG. 7 is a diagram illustrating one example of a notification screen 83 displayed on the display 125 according to the present embodiment. The display controlling function 123h displays on the notification screen 83, a locator image 821b imaged by the pre-scanning and a message M3a notifying that resetting is recommended. The locator image 821a and the locator image 821b are simply referred to as the locator image 821 unless they need to be distinguished.

In the example illustrated in FIG. 7, the display controlling function 123h displays on the notification screen 83, a message M3b suggesting the contents of the correction of the setting. The content and the display position of the messages M3a and M3b are illustrated as one example here and not limited to those in FIG. 7.

The display controlling function 123h displays a resetting button 23 on the notification screen 83. With the resetting button 23, the operator can input the desire to perform another pre-scanning after resetting the subject P or the local RF coil 130. Moreover, the display controlling function 123h displays an imaging button 24, with which the operator can input the desire to continue the imaging, on the notification screen 83.

Next, the procedure of the imaging assist process performed by the MRI apparatus 100 with the above structure is described.

Figure 8B:
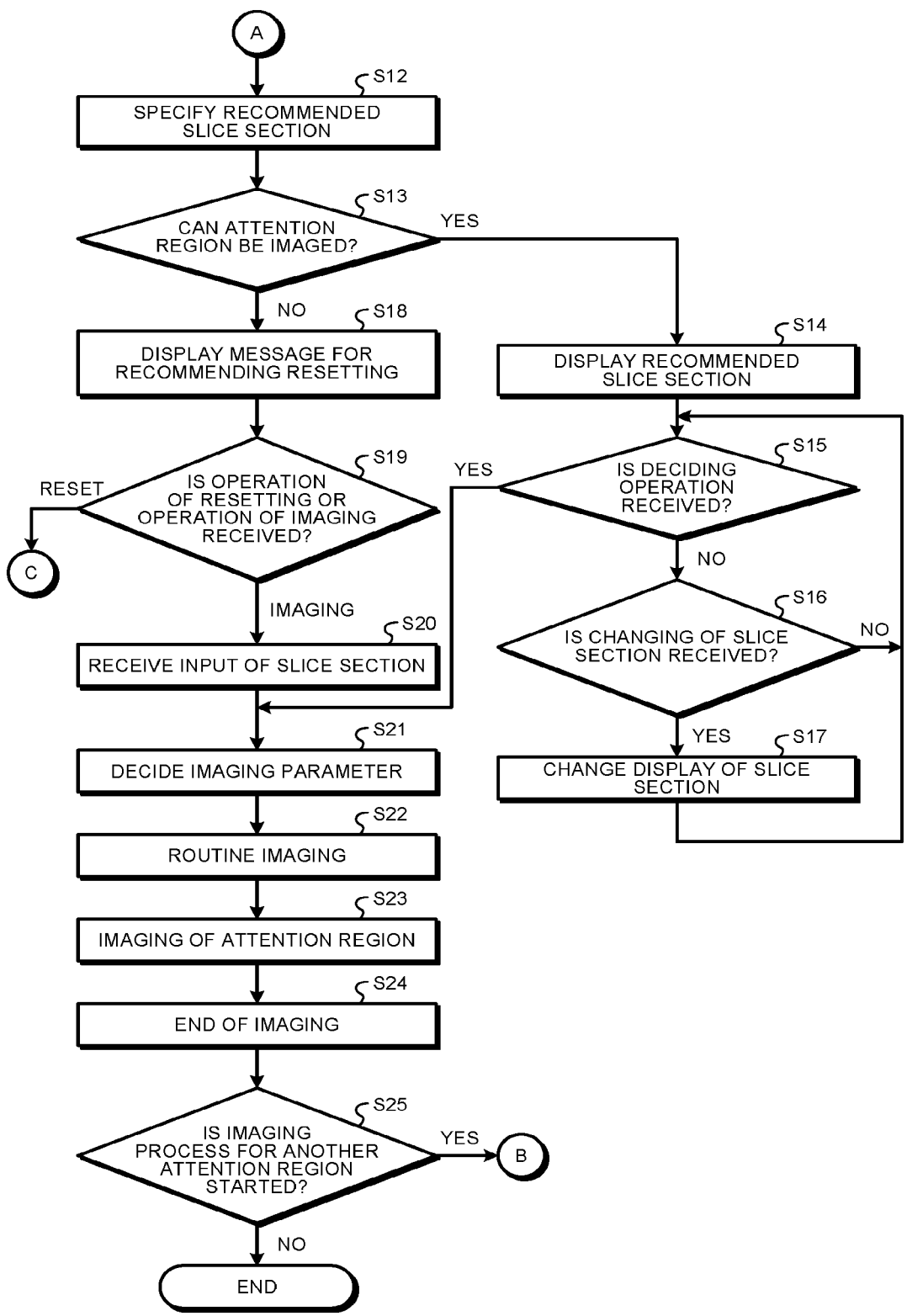
FIG. 8B is a continuation of the flowchart illustrated in FIG. 8A.

FIGS. 8A and 8B are a flowchart illustrating one example of the procedure of the imaging assist process according to the present embodiment.

First, the acquiring function 123d acquires the patient information of the subject P from HIS or RIS, for example, through the network interface 121 (S1). The acquiring function 123d sends the acquired patient information to the collecting function 123a.

The acquiring function 123d acquires the information about the disease or the case of the subject P through the network interface 121 (S2). The acquiring function 123d sends the acquired information about the disease or the case of the subject P to the estimating function 123e.

Next, the receiving function 123c receives the input of the FOV from the operator through the input interface 124 (S3). The receiving function 123c sends the received FOV to the collecting function 123a.

Next, the estimating function 123e estimates one or more candidates for the attention region from the information about the disease or the case (S4). The estimating function 123e sends the estimated one or more candidates for the attention region to the display controlling function 123h.

The display controlling function 123h displays one or more selection buttons 20 corresponding to the one or more candidates for the attention region on the attention region selecting screen 80 described with reference to FIG. 4 (S5).

Then, the receiving function 123c receives the operator's input of the attention region through the input interface 124 (S6). Specifically, the receiving function 123c receives the operator's operation of selecting one selection button 20 on the attention region selecting screen 80 through the input interface 124.

Next, the display controlling function 123h causes the display 125 to display the setting assisting screen 81 (S7).

Then, the receiving function 123c receives the input of the completion of the setting by the operator through the input interface 124 (S8).

Next, the acquiring function 123d acquires the captured image from the camera 30 through the network interface 121 (S9).

Then, the display controlling function 123h causes the display 125 to display the acquired captured image (S10). By recognizing the captured image visually, the operator checks the posture of the subject P or the attaching state of the local RF coil 130.

After checking the posture of the subject P or the attaching state of the local RF coil 130, the operator inputs the operation of starting the pre-scanning to the input interface 124. Then, the collecting function 123a performs the pre-scanning by controlling the sequence control circuitry 110 through the network interface 121 (S11).

Then, after the subject P is pre-scanned, the specifying function 123f specifies the position of the slice section associated with the attention region received by the input interface 124 on the basis of the imaging assistant information 90 (S12).

Next, the determining function 123g determines whether the attention region can be imaged (S13). For example, when the recommended slice section specified by the specifying function 123f can be set on the attention region of the subject P drawn on the locator image 821 that is imaged in the pre-scanning, the determining function 123g determines that the attention region can be imaged (Yes at step S13).

In this case, the display controlling function 123h causes the display 125 to display the slice decision assisting screen 82 (S14). As described with reference to FIG. 6, the display controlling function 123h displays, on the slice decision assisting screen 82, the slice reference image 822 expressing the recommended slice section, the message M2 describing the recommended slice section, and the decision button 22 on the locator image 821a.

Then, the receiving function 123c determines whether the operator's operation of deciding the slice section is received through the input interface 124 (S15). The operation of deciding the slice section is, for example, pushing the decision button 22.

If the changing of the slice section by the operator is received (Yes at S16) while it is not determined that the operation of deciding the slice section is received (No at S15), the receiving function 123c sends the received content of the operation of changing the slice section to the display controlling function 123h.

In this case, the display controlling function 123h changes the position, the thickness, or the tilt of the slice reference image 822 displayed on the slice decision assisting screen 82 in accordance with the operator's operation (S17). Then, back to the process at S15, if it is determined that the operation of deciding the slice section is received (Yes at S15), the receiving function 123c advances the process to S21. Note that the process returns to S15 also when the changing of the slice section by the operator is not received (No at S16).

When the recommended slice section specified by the specifying function 123f cannot be set on the attention region of the subject P drawn on the locator image 821 that is imaged in the pre-scanning, the determining function 123g determines that the attention region cannot be imaged (No at step S13).

In this case, the display controlling function 123h causes the display 125 to display the notification screen 83 (S18). As described with reference to FIG. 7, the display controlling function 123h displays, on the notification screen 83, the locator image 821b, the message M1a notifying that the resetting is recommended, the message M3b suggesting the contents of the correction of the setting, the resetting button 23, and the imaging button 24.

Then, the receiving function 123c determines which one of the resetting and the continuation of the imaging by the operator is received (S19).

When the pushing of the resetting button 23 is received through the input interface 124, the receiving function 123c determines that the operator's resetting operation is received ("reset" at S19). In this case, back to the process at S7, the display controlling function 123h causes the display 125 to display the setting assisting screen 81.

The receiving function 123c determines that the operator's operation of continuing the imaging is received when the pushing of the imaging button 24 is received through the input interface 124 ("imaging" at S19). In this case, for example, the receiving function 123c receives the operator's operation of inputting the slice section (S20).

Next, the collecting function 123a decides the imaging parameter on the basis of the FOV and the attention region received by the receiving function 123c, the patient information acquired by the network interface 121, and the position, the slice thickness, and the tilt of the recommended slice section specified by the specifying function 123f or the slice section input by the operator (S21). Then, the collecting function 123a generates the sequence information on the basis of the decided imaging parameter.

In addition, here, the collecting function 123a performs routine imaging in the FOV received by the receiving function 123c (S22). The routine imaging is a series of MR imaging that is determined in advance for each imaging part, for example, and a plurality of magnetic resonance images are imaged while the contrast or the slice section is changed. Note that the routine imaging is optional, and therefore S22 may be skipped and the next process at S23 may be performed.

Then, the collecting function 123a performs the imaging of the attention region by sending the sequence information generated based on the imaging parameter generated at S21 to the sequence control circuitry 110 through the network interface 121 (S23).

Moreover, the collecting function 123a collects the MR data, which is converted from the MR signal generated from the subject P, from the sequence control circuitry 110 through the network interface 121. After the collection of the MR data is completed, the imaging ends (S24).

Here, the reconstructing function 123b may generate a magnetic resonance image corresponding to a result of imaging of the attention region. In this case, the display controlling function 123h may cause the display 125 to display the generated magnetic resonance image.

Then, the receiving function 123c determines whether the operator's operation of starting the imaging process for another attention region is received through the input interface 124 (S25).

When the receiving function 123c has determined that the operator's operation of starting the imaging process for another attention region is received (Yes at S25), the process returns to S5. In this case, the display controlling function 123h displays the attention region selecting screen 80 again.

When the receiving function 123c has determined that the operator's operation of not starting the imaging process for another attention region is received (No at S25), the process in this flowchart ends.

In this manner, the MRI apparatus 100 according to the present embodiment causes the display 125 to display the posture information suitable to perform imaging of the disease or the case of the subject P that is associated with the attention region about the disease or the case of the subject P. By seeing the display, the technologist can find the posture suitable to perform imaging of the disease or the case of the subject P; therefore, it becomes easier to set the subject P. For this reason, the MRI apparatus 100 according to the present embodiment can provide the information about the suitable posture that the subject P should have at the imaging time. The technologist can fix the subject P at the position suitable to the imaging by referring to the provided information.

The posture information according to the present embodiment expresses the posture of the subject P that enables the imaging of the attention region included in the FOV. Therefore, even in the case where whether the imaging of the attention region is possible depends on the posture of the subject P, the MRI apparatus 100 according to the present embodiment can support the technologist to fix the subject P with the posture that enables the imaging of the attention region.

More specifically, the posture information according to the present embodiment is the information about the posture of the joint part of the subject P, and for example, is the information expressing the bending angle of the joint of the subject P. For example, in order to image the damage in the ligament or the like, the joint may need to be bent for a predetermined angle or more. The MRI apparatus 100 according to the present embodiment can support the technologist to fix the joint of the subject P at the angle suitable to the imaging by causing the display 125 to display the information about the posture of the joint part of the subject P suitable to perform imaging of the disease or the case, for example the information expressing the bending angle of the joint of the subject P in accordance with the disease or the case of the subject P.

The MRI apparatus 100 according to the present embodiment specifies the position of the slice section associated with the attention region received by the input interface 124 from the imaging assistant information 90, and causes the display 125 to display the specified position of the slice section. Thus, the MRI apparatus 100 according to the present embodiment can support the operator to set the position of the slice section where the attention region of the subject P can be imaged.

The MRI apparatus 100 according to the present embodiment specifies the slice thickness or the tilt of the slice section associated with the attention region received by the input interface 124 from the imaging assistant information 90, and causes the display 125 to display the specified slice thickness or tilt of the slice section. Thus, the MRI apparatus 100 according to the present embodiment can support the operator to set the slice thickness or the slice section that enables the imaging of the attention region of the subject P.

The MRI apparatus 100 according to the present embodiment causes the display 125 to display one or more selection buttons 20 expressing one or more attention regions in accordance with the disease or the case of the subject P, and receives the operator's input of the attention region from the one or more selection buttons 20. Thus, when the attention regions about the disease or the case of the subject P exist, the MRI apparatus 100 according to the present embodiment enables the operator to select the attention region to be the object of the imaging easily.

In addition, the MRI apparatus 100 according to the present embodiment causes the display 125 to display the posture information before the imaging process is performed. The imaging process includes the pre-scanning and the imaging. By the MRI apparatus 100 according to the present embodiment, the technologist can find the posture of the subject P suitable to perform imaging of the attention region before the imaging; therefore, it is possible to avoid performing the setting again after the imaging or to reduce the trial and error for the technologist.

Note that in the present embodiment, the MRI apparatus 100 includes the local RF coil 130; however, this structure is one example, and the MRI apparatus 100 may exclude the local RF coil 130. Alternatively, the MRI apparatus 100 may include the local RF coils 130.

In the present embodiment, the imaging assistant information 90 and the attention region candidate information 91 are saved in the storage 122; however, the imaging assistant information 90 and the attention region candidate information 91 may be stored not in the storage 122 but in an external storage device.

In the present embodiment, the FOV is received by the input interface 124; however, the method of acquiring the FOV by the MRI apparatus 100 is not limited to this method. For example, the FOV may be acquired through the network interface 121 from an external device connected to the MRI apparatus 100 with a hospital intranet or the like.

In addition to the FOV, various pieces of information may be acquired from other than the input interface 124. In this case, the receiving function 123c, the acquiring function 123d, or the network interface 121 may be one example of the input interface.

In the present embodiment, the acquiring function 123d is one example of the acquirer; however, the network interface 121 may be one example of the acquirer.

In the present embodiment, the specifying function 123f specifies the position of the slice section, the slice thickness, and the tilt of the slice section; however, the specifying function 123f does not need to specify all these three pieces of information. For example, the specifying function 123f may specify one or two of these three pieces of information.

First Modification

In the aforementioned embodiment, the MRI apparatus 100 is one example of the imaging support apparatus; however, the imaging support apparatus is not limited to the MRI apparatus 100. For example, the MRI apparatus 100 may be a personal computer (PC) or a server that is provided separately from the MRI apparatus 100. In the case of using this structure, the imaging support apparatus is connected to and communicates with the MRI apparatus 100 through the hospital intranet or the like; thus, the imaging assist process is performed.

Second Modification

In the aforementioned embodiment, the FOV is one example of the region to be excited; however, the region to be excited is not limited to the FOV. For example, a region where an inversion recovery (IR) pulse or a saturation (SAT) pulse is applied may be one example of the region to be excited. In addition to the IR pulse and the SAT pulse, a region where various prepulses are applied may be used as the region to be excited.

In this case, the posture information expresses the posture of the subject P that is suitable to excite the region where various prepulses are applied. For example, in the case where various prepulses are applied to the subject P, the posture that the subject P should have may be different depending on the disease or the case of the subject P. In this modification, in the case where various prepulses are applied, the technologist can be supported to fix the subject P with the suitable posture.

Third Modification

In the aforementioned embodiment, the information expressing the attention region is one example of the first information; however, the first information is not limited to this example. In this modification, the information about the disease or the case of the subject P is one example of the first information.

In the aforementioned embodiment, the imaging assistant information 90 and the attention region candidate information 91 are stored in different tables as described with reference to FIG. 2 and FIG. 3; however, the imaging assistant information may include the attention region candidate information.

FIG. 9 is a diagram illustrating one example of imaging assistant information 1090 according to the present modification. As illustrated in FIG. 9, in the imaging assistant information 1090, which is one example of the second information, the information about the disease or the case of the subject P corresponding to one example of the first information and the posture information are associated with each other.

In the present modification, the specifying function 123*f* may have the function of the aforementioned estimating function 123*e*.

Fourth Modification

In the aforementioned embodiment, the MRI apparatus 100 receives the operator's input of the FOV from the input interface 124; however, the method of deciding the FOV is not limited to this example. For example, the collecting function 123*a* may decide the FOV including the attention region in accordance with the decided attention region.

Fifth Modification

In the aforementioned embodiment, the attention region is input when the operator pushes the selection button 20; however, the attention region may be input as text information by the operator.

In the present modification, the specifying function 123*f* is a search engine that searches the imaging assistant information 90 or the imaging assistant information 1090 for the posture information corresponding to the attention region on the basis of the attention region input as the text information.

In other words, the processing circuitry 123 according to the present modification includes the search engine.

Sixth Modification

In the aforementioned embodiment, the information about the disease or the case of the subject P is acquired by the network interface 121; however, the information about the disease or the case of the subject P may be input as the text information by the operator.

In the present modification, the input interface 124 receives as the text information, the information about the disease or the case of the subject P input by the operator.

In the present modification, the estimating function 123*e* or the specifying function 123*f* is a search engine that searches the attention region candidate information 91 or the imaging assistant information 1090 for the posture information corresponding to the information about the disease or the case on the basis of the information about the disease or the case of the subject P input as the text information. In other words, the processing circuitry 123 according to the present modification includes the search engine. In the present modification, the display controlling function 123*h* causes the display 125 to display the posture information obtained by the search engine.

Seventh Modification

In the aforementioned embodiment, the network interface 121 acquires the information about the disease or the case of the subject P; however, the estimating function 123*e* may estimate the disease or the case of the subject P from a moving picture in which the subject P walks, for example. In this case, this moving picture corresponds to the information about the disease or the case of the subject P.

The moving picture in which the subject P walks may be, for example, the moving picture captured by the camera 30 or obtained by another image capture device.

Any of the first to seventh modifications described above may be employed alone or two or more of these modifications may be combined with each other.

By at least one embodiment described above, the technologist can be supported to fix the patient with the suitable posture in the imaging.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An imaging support apparatus comprising:
   processing circuitry configured to,
   acquire input of information expressing a field of view of a subject and one of a plurality of pieces of first information, each of the plurality of pieces of first information indicating an attention region to which attention is paid for diagnosing a disease or a case of the subject, the attention region being narrower than the field of view,
   specify one of a plurality of pieces of posture information corresponding to the acquired one of the plurality of pieces of first information on basis of second information, wherein the second information has the plurality of pieces of first information and the plurality of pieces of posture information associated with each other in advance, each of the plurality of pieces of posture information indicating information about a posture of a joint part of the subject expressed by text information or image data, each of the plurality of pieces of posture information being specified based on the associated one of the plurality of pieces of first information, each of the plurality of pieces of posture information expressing a posture of the subject that enables imaging of the disease or the case indicated by the associated one of the plurality of pieces of first information in the field of view of the subject, and cause a display to display the specified one of the plurality of pieces of posture information, wherein the plurality of pieces of first information, the plurality of pieces of posture information, and a plurality of pieces of imaging surface information are associated with each other in the second information, each of the plurality of pieces of imaging surface information indicating information about an imaging surface in imaging of the subject, each of the plurality of pieces of imaging surface information expresses a position of a slice section in the imaging of the subject, and the processing circuitry is configured to specify a position of a slice section associated with the acquired one of the plurality of pieces of first information, from the second information, cause the display to display the specified position of the slice section when it is determined that imaging of the attention region is possible on basis of a posture of the subject and a sensitivity of a coil in a pre-scanning that is performed before the imaging of the subject, the coil receiving a magnetic resonance signal generated from the subject due to influence of a high-frequency magnetic field, and cause the display to display a notification screen to notify that imaging of the attention region is impossible when it is determined that imaging of the attention region is impossible on basis of the posture of the subject and the sensitivity of the coil in the pre-scanning.

2. The imaging support apparatus according to claim 1, wherein each of the plurality of pieces of posture information expresses the posture of the subject that enables imaging of the attention region included in the field of view indicated by the associated one of the plurality of pieces of first information.

3. The imaging support apparatus according to claim 1, wherein the posture information about the posture of the joint part of the subject is information expressing a bending angle of a joint of the subject.

4. The imaging support apparatus according to claim 1, wherein each of the plurality of pieces of imaging surface information further includes information about a slice thickness, the processing circuitry being configured to specify a slice thickness associated with the acquired one of the plurality of pieces of first information from the second information, and cause the display to display information expressing the specified slice thickness.

5. The imaging support apparatus according to claim 1, wherein each of the plurality of pieces of imaging surface information further includes information about a tilt of the slice section, the processing circuitry being configured to specify a tilt of the slice section associated with the acquired one of the plurality of pieces of first information, from the second information, and cause the display to display information expressing the specified tilt of the slice section.

6. The imaging support apparatus according to claim 1, wherein the processing circuitry is configured to cause the display to display one or more buttons expressing one or more candidates for an attention region in accordance with the disease or the case of the subject, and acquire input of the attention region by an operator from the one or more buttons.

7. The imaging support apparatus according to claim 1, wherein the processing circuitry is configured to acquire one of the plurality of pieces of first information input by an operator as text information, the processing circuitry includes a search engine that searches the second information for one of the plurality of pieces of posture information corresponding to the acquired one of the plurality of pieces of first information on basis of the text information, and the processing circuitry is configured to cause the display to display the one of the plurality of pieces of posture information obtained by the search engine.

8. The imaging support apparatus according to claim 1, wherein the processing circuitry is configured to cause the display to display the specified one of the plurality of pieces of posture information before an imaging process.

9. A magnetic resonance imaging apparatus comprising an imaging support apparatus and an RF coil configured to excite a subject, the imaging support apparatus comprising:

processing circuitry configured to acquire input of information expressing a field of view of a subject and one of a plurality of pieces of first information, each of the plurality of pieces of first information indicating an attention region to which attention is paid for diagnosing a disease or a case of the subject, the attention region being narrower than the field of view, specify one of a plurality of pieces of posture information corresponding to the acquired one of the plurality of pieces of first information on basis of second information, wherein the second information has the plurality of pieces of first information and the plurality of pieces of posture information associated with each other in advance, each of the plurality of pieces of posture information indicating information about a posture of a joint part of the subject expressed by text information or image data, each of the plurality of pieces of posture information being specified based on the associated one of the plurality of pieces of first information, each of the plurality of pieces of posture information expressing a posture of the subject that enables imaging of the disease or the case indicated by the associated one of the plurality of pieces of first information in the field of view of the subject, and cause a display to display the specified one of the plurality of pieces of posture information, wherein each of the plurality of pieces of posture information expresses the posture of the subject suitable to excite a region to be excited, the plurality of pieces of first information, the plurality of pieces of posture information, and a plurality of pieces of imaging surface information are associated with each other in the second information, each of the plurality of pieces of imaging surface information indicating information about an imaging surface in imaging of the subject, each of the plurality of pieces of imaging surface information expresses a position of a slice section in the imaging of the subject, and the processing circuitry is configured to specify a position of a slice section associated with the acquired one of the plurality of pieces of first information, from the second information, cause the display to display the specified position of the slice section when it is determined that imaging of the attention region is possible on basis of a posture of the subject and a sensitivity of a coil in a pre-scanning that is performed before the imaging of the subject, the coil receiving a magnetic resonance signal generated from the subject due to influence of a high-frequency magnetic field, and cause the display to display a notification screen to notify that imaging of the attention region is impossible when it is determined that imaging of the attention region is impossible on basis of the posture of the subject and the sensitivity of the coil in the pre-scanning.

10. An imaging support method comprising:

acquiring input of information expressing a field of view of a subject and one of a plurality of pieces of first information, each of the plurality of pieces of first information indicating an attention region to which attention is paid for diagnosing a disease or a case of the subject, the attention region being narrower than the field of view;

specifying one of a plurality of pieces of posture information corresponding to the acquired one of the plurality of pieces of first information on a basis of second information, wherein the second information has the plurality of pieces of first information and the plurality of pieces of posture information associated with each other in advance, each of the plurality of pieces of posture information indicating information about a posture of a joint part of the subject expressed by text information or image data, each of the plurality of pieces of posture information being specified based on the associated one of the plurality of pieces of first information, each of the plurality of pieces of posture information expressing a posture of the subject that enables imaging of the disease or the case indicated by the associated one of the plurality of pieces of first information in the field of view of the subject; and causing a display to display the specified one of the plurality of pieces of posture information, wherein the plurality of pieces of first information, the plurality of pieces of posture information, and a plurality of pieces of imaging surface information are associated with each other in the second information, each of the plurality of pieces of imaging surface information indicating information about an imaging surface in imaging of the subject, each of the plurality of pieces of imaging surface information expresses a position of a slice section in the imaging of the subject, the method further comprising specifying a position of a slice section associated with the acquired one of the plurality of pieces of first information, from the second information, causing the display to display the specified position of the slice section when it is determined that imaging of the attention region is possible on basis of a posture of the subject and a sensitivity of a coil in a pre-scanning that is performed before the imaging of the subject, the coil receiving a magnetic resonance signal generated from the subject due to influence of a high-frequency magnetic field, and causing the display to display a notification screen to notify that imaging of the attention region is impossible when it is determined that imaging of the attention region is impossible on basis of the posture of the subject and the sensitivity of the coil in the pre-scanning.

11. The imaging support apparatus according to claim 1, wherein either the acquired one of the plurality of pieces of first information acquired or the acquired information expressing the field of view of the subject includes information received by an input interface, or both the acquired one of the plurality of pieces of first information acquired and the acquired information expressing the field of view of the subject include information received by the input interface.

12. The imaging support apparatus according to claim 1, wherein the field of view of the subject is a region to be excited by magnetic resonance imaging of the subject.

13. An imaging support apparatus comprising:

processing circuitry configured to acquire input of information expressing a field of view of a subject and one of a plurality of pieces of first information, each of the plurality of pieces of first information indicating an attention region to which attention is paid for diagnosing a disease or a case of the subject, the attention region being narrower than the field of view, specify one of a plurality of pieces of posture information corresponding to the acquired one of the plurality of pieces of first information on basis of second information, wherein the second information has the plurality of pieces of first information and the plurality of pieces of posture information associated with each other in advance, each of the plurality of pieces of posture information indicating information about a posture of a joint part of the subject expressed by text information or image data, each of the plurality of pieces of posture information being specified by the associated one of the plurality of pieces of first information, each of the plurality of pieces of posture information expressing a posture of the subject that enables imaging of the disease or the case indicated by the associated one of the plurality of pieces of first information in the field of view of the subject, and cause a display to display the specified one of the plurality of pieces of posture information, wherein the plurality of pieces of first information, the plurality of pieces of posture information, and a plurality of pieces of imaging surface information are associated with each other in the second information, each of the plurality of pieces of imaging surface information indicating information about an imaging surface in imaging of the subject, each of the plurality of pieces of imaging surface information expresses a position of a slice section in the imaging of the subject, and the processing circuitry is configured to specify a position of a slice section associated with the acquired one of the plurality of pieces of first information, from the second information, acquire a locator image generated by a pre-scanning that is performed before the imaging of the subject, cause the display to display the specified position of the slice section when it is possible to form the specified slice section on the locator image, and cause the display to display a notification screen to notify that imaging of the attention region is impossible when it is impossible to form the specified slice section on the locator image.

* * * * *